United States Patent [19]
Romano' et al.

[11] Patent Number: 5,752,941
[45] Date of Patent: May 19, 1998

[54] CENTRAL VENOUS CATHETERS LOADED WITH ANTIBIOTICS OF THE RAMOPLANIN GROUP PREVENTING DEVELOPMENT OF CATHETER RELATED INFECTIONS

[75] Inventors: Gabriella Romano', Legnano, Italy; Beth P. Goldstein, Tarrytown, N.Y.; Rosamund Jean Williams, Saronno, Italy; Maurizio Denaro, Del Mar, Calif.

[73] Assignee: Gruppo Lepetit S.p.A., Italy

[21] Appl. No.: 687,413

[22] PCT Filed: Feb. 1, 1995

[86] PCT No.: PCT/EP95/00355

§ 371 Date: Aug. 2, 1996

§ 102(e) Date: Aug. 2, 1996

[87] PCT Pub. No.: WO95/21636

PCT Pub. Date: Aug. 17, 1995

[30] Foreign Application Priority Data

Feb. 15, 1994 [IT] Italy .................................. 94102280.8

[51] Int. Cl.$^6$ .......................... A61M 5/35; A61M 25/00
[52] U.S. Cl. ........................................................ 604/265
[58] Field of Search .................. 604/49, 513, 264–266, 604/280, 890.1; 623/1

[56] References Cited

U.S. PATENT DOCUMENTS

| | | | |
|---|---|---|---|
| 4,769,013 | 9/1988 | Lorenz et al. | 604/265 |
| 4,950,256 | 8/1990 | Luther et al. | 604/265 |
| 5,344,411 | 9/1994 | Domb et al. | 604/265 |
| 5,445,609 | 8/1995 | Lattin et al. | 604/20 |
| 5,533,971 | 7/1996 | Phipps | 604/20 |

FOREIGN PATENT DOCUMENTS

| | | |
|---|---|---|
| 0590348 | 4/1994 | European Pat. Off. |

OTHER PUBLICATIONS

Feld et al., Medical and Pediatric Oncology, 1:175–181 (1975): "Intravenous Catheter Infection Study: A Prospective Trial in Patients With Neoplastic Disease".

Evans et al., Antimicrob. Agents Chemother., 31(6):889–894, (1987) "Effect of Vancomycin Hydrochloride on Staphylococcus epidermidis Biofilm Associated with Silicone Elastomer".

Gristina et al., Antimicrob. Agents Chemother., 33(6):813–813, (1989) "Comparative In–Vitro Antibiotic Resistance of Surface–Colonizing Coagulase–Negative Staphylococci".

Sheth et al., The Lancet. 1266–1286. Dec. 7, 1985. "Influence of Bacterial Adherence to Intravascular Catheters on In–Vitro Antibiotic Susceptibility".

Jansen et al., Polym. Mater. Sci. Eng. 59:794–797 (1988). "Antibiotic–Containing Polyurethanes for the prevention of Foreign–Body Infections".

Jansen et al., J. of Investigative Surgery, 2:361–380 (1989). "New Aspects in the Pathogenesis and Prevention of Polymer–Associated Foreign–Body Infections Caused by Coagulase–Negative Staphylococci".

Jannsen et al., J. of Hospital Infection, 19:83–88, (1991). "Modern straegies in the prevention of polymer–associated infections".

Cheng Huaijin, Eur. Urol., 14:72–74 (1988). "Manufacture and Clinical Employment of an Antibiotic Silicon–Rubber Catherter".

Sakamoto et al., J. of Biomedical Materials Research, 19:1031–1041 (1985). "Efficacy of an antibiotic coated indwelling catheter: A preliminary report".

Sherertz et al. Antimicrob. Agents Chemother., 33(8):1174–1178, (1989) Efficacy of Dicloxacillin–Coated Polyurethane Catheters in Preventing Subcutaneous *Staphylococcus aureus* Infection in Mice.

Trooskin et al., Surgery, 97(5):547–551 (1985). "Prevention of catherter sepsis by antibiotic bonding".

Trooskin et al., Nephron, 46–263–267 (1987). "Infection–Resistant Continuous Peritoneal Dialysis Catherter".

Kamal et al., JAMA, 265(18);2364–2368, (1991) "Reduced Intravascular Catheter Infection by Antibiotic Bonding".

Jansen, B. et al., J. Hosp. Infect., 22:93–107, (1992) "In–vitro efficacy of a central venous catheter ('Hydrocath') loaded with tricoplanin to prevent bacterial colonization".

*Primary Examiner*—Mark Bockelman
*Assistant Examiner*—Jennifer R. Sadula
*Attorney, Agent, or Firm*—Killworth, Gottman, Hagan & Schaeff, L.L.P.

[57] ABSTRACT

The invention relates to central venous polyurethane catheters with a thin hydrophilic coating loaded with an antibiotic of the ramoplanin group or any mixture thereof and their use in preventing catheter related infections. These catheters are useful to prevent bacterial adherence and colonization and, therefore, to lower the risk of vascular infections in catheterized patients. The method of preparing the catheter of the invention consists in incubating polyurethane catheters coated with a hydrophilic film in an aqueous solution of the selected antibiotic.

13 Claims, No Drawings

CENTRAL VENOUS CATHETERS LOADED WITH ANTIBIOTICS OF THE RAMOPLANIN GROUP PREVENTING DEVELOPMENT OF CATHETER RELATED INFECTIONS

This invention relates to central venous polyurethane catheters with a thin hydrophilic coating loaded with an antibiotic of the ramoplanin group, the method for their preparation and their use in preventing development of catheter related infections in patients.

The catheters of this invention are useful to prevent bacterial adherence and colonization and, therefore, to lower the risk of vascular infections in catheterized patients.

Infections of central venous lines represent a challenging problem in modern medicine (1-4). Contamination of the catheter by skin flora during insertion is thought to be one of the major routes in the development of catheter infections. Gram-positive bacteria like Staphylococcus aureus and coagulase negative staphylococci (CNS) are the predominant causative organisms.

Catheter infections may lead to severe complications for a patient, and, even if they are not life-threatening, they may contribute to a prolongation of hospital stay and to an increase in therapy costs. Most of the catheter infections can be managed by removing the catheter if clinical signs of infection occur; this is normal clinical routine procedure in patients having short peripheral venous lines.

In cases of difficulties for venous access, however, and especially in patients with a long-term central venous catheter, keeping the catheter in place despite the infection is desired. In many cases, however, antibiotic therapy is not able to eliminate bacteria from the catheter.

The failure of antibiotic therapy is mainly due to the existence of a slime barrier (biofilm) which hinders the antibiotic in penetrating and in reaching the adherent bacterial cells.

It was discovered by many investigators that the MIC- or MBC-values of antibiotics for bacteria embedded in a biofilm are much higher than those for bacteria in suspension (5, 6, 7).

An alternative strategy to treat and especially to prevent catheter infections is the coating or loading of medical devices with antimicrobial substances (8-10). The release of the antimicrobial substance (e.g. an antibiotic) from the catheter surface or from the interior leads to a high local drug concentration which should be sufficiently high to reach the MIC and MBC of bacteria in biofilms. Furthermore, local antimicrobial action shortly after catheter insertion would probably inhibit the production of a biofilm by the bacteria. There are already a number of investigations on the coating or loading of catheter materials with antimicrobial substances, mainly with antibiotics (11-15, 16). Such systems show in part good in vitro performances; in a few cases there have already been clinical trials with antimicrobial-coated catheters (11, 17).

Development of resistance to commonly used antibiotics, for instance, due to resistant Staphylococcus aureus strains (see M. E. Reverdy et al., "Evolution de la résistance aux antibiotiques et aux antiseptiques de souches hospitalières de Staphylococcus aureus isolées de 1980 à 1991" published in Pathologie Biologie, 1993, Vol. 41, No. 9 897–904), is a further factor which makes difficult the management of infections in hospitals and favors any possible employment of antibiotics not yet utilized in the clinical practice.

The main object of this invention is to provide a central venous polyurethane catheter with a thin hydrophilic layer on the surfaces loaded with an antibiotic of the ramoplanin group or any mixture thereof, in a concentration sufficient to inhibit the bacterial colonization of the catheter after its insertion into the patient. The catheters of this invention can be maintained in place for the desired period without incurring severe complications for the catheterized patient.

According to in vitro experiments described by B. Jansen et al. (18), it has been found that teicoplanin has appropriate biological and physico-chemical characteristics to allow absorption on the thin hydrophilic layer coating the surfaces of certain central venous polyurethane catheters. The release of antibacterially active concentrations of the substance in an elution fluid is taken as an effect which may be correlated with the prevention of the bacterial colonization of the catheter and, therefore, the development of an infection in a patient.

Following the generic indications given by the same authors, the glyco or lipopeptide antibiotics such as vancomycin, daptomycin and ramoplanin would not appear to be useful for the preparation of central venous catheters preventing the catheter related infections in view of their poor absorption/release properties.

According to this invention, it has been surprisingly discovered that the central venous polyurethane catheters with a thin hydrophilic layer on the surfaces loaded with an antibiotic of the ramoplanin group or any mixture thereof, are effective in inhibiting development of bacterial colonization and preventing catheter related infections after the insertion into the patients.

Therefore, a further object of this invention is a method of preventing catheter related infections in a patient in need of application of a central venous catheter, such method consisting in the insertion into the patient of a central venous polyurethane catheter with a thin hydrophilic layer on the surfaces loaded with an antibiotic of the ramoplanin group or any mixture thereof.

Ramoplanin is an International Non-Proprietary Name which identifies the antibiotic complex originally designated as A/16686.

Antibiotic A/16686 is an antibiotic produced by Actinoplanes sp. ATCC 33076 active against aerobic and anaerobic gram-positive bacteria, including methicillin-resistant Staphylococci and bacteria resistant to ampicillin and erythromicin and it is described in U.S. Pat. 4,303,646 together with its manufacture process and pharmaceutical composition containing it.

Preliminary physico-chemical characterization indicated by Cavalleri et al. (19) that antibiotic A/16686 is formed by a peptidic core carrying two D-mannose units.

It was then found that three closely related major components could be isolated from antibiotic A/16686 which were named factor A1, A2 and A3. Factor A2 is the component obtained in preponderant amount and is the most relevant for the biological activity, while factor A1 and A3 are obtained in a minor amount. These substances as well as their preparation and uses are described in U.S. Pat. 4,427,656.

It is however possible to modulate the proportion of the three above major components in the complex obtained by fermentation of the microorganism Actinoplanes sp. ATCC 33076. In fact, a method for selectively enhancing the production of factors A2 and/or A3 of antibiotic A/16686 by adding appropriate precursors to an A/16686 producing culture, is described in European Patent Application Publication No. 259780.

Recent studies showed that these three factors have a common cyclic depsipeptide skeleton composed by seventeen aminoacids and a dimannosyl unit. Three different unsaturated fatty acid residues differentiate the three components of the complex.

The antibiotics characterized by the simultaneous presence of a depsipeptide skeleton, fatty acids and sugar moieties have been defined in the scientific literature as glycolipodepsipeptide antibiotics (20).

The following formula I can be suggested for the three closely related components of antibiotic A/16686:

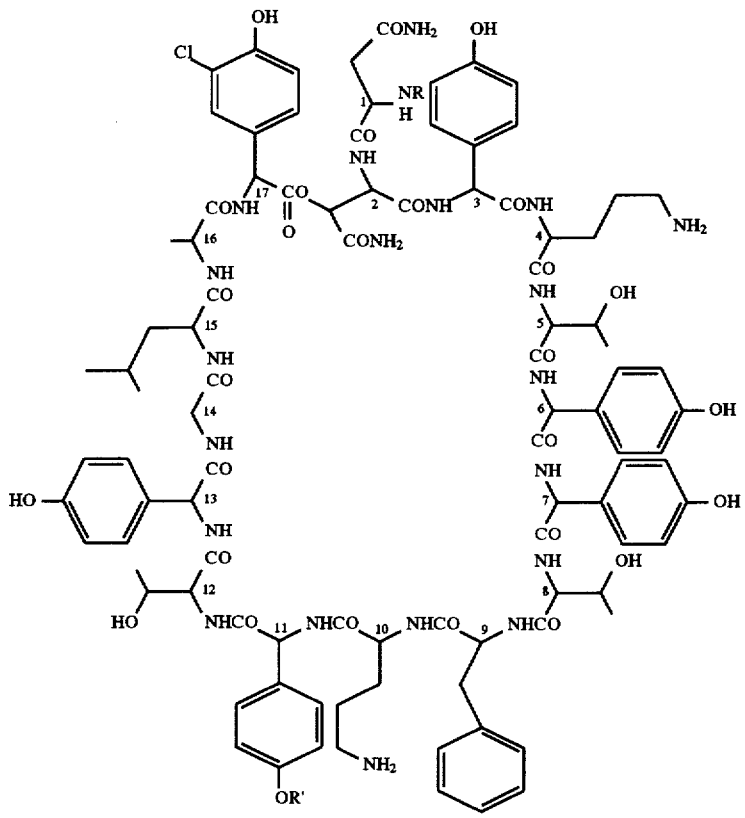

wherein:

R is: —CO—CH=CH—CH=CH—CH$_2$—CH$_2$—CH$_3$, —CO—CH=CH—CH=CH—CH$_2$—CH(CH$_3$)$_2$ or —CO—CH=CH—CH=CH—CH$_2$—CH$_2$—CH(CH$_3$)$_2$ and R' is a dimannosyl moiety.

European Patent Application Publication No. 318680 describes other compounds related to antibiotic A/16686 complex.

Said compounds, named factors A'1, A'2 and A'3 respectively, are produced by Actinoplanes sp. ATCC 33076 under appropriate conditions and correspond to factors A1, A2 and A3 of formula I wherein R' is a mannosyl moiety.

Catalytic hydrogenation of each of the factors A and/or A' or their mixtures, yields the corresponding derivatives tetrahydrogenated in the fatty acid chain portions. European Patent Application Publication No. 321696 describes the tetrahydrogenated derivatives of the several factors A and A' of A/16686 complex and mixtures thereof and their method of manufacture.

European Patent Application Publication No. 337203 describes the obtainment of the aglycons of the components of the A/16686 antibiotic complex and their derivatives hydrogenated in the fatty acid chain portions. The cleavage of the glycosyl moiety is achieved by selective hydrolysis.

In this description and claims the term "antibiotic of the ramoplanin group" identifies any single factor of the A/16686 complex and any derivative thereof among those described above.

The expression "any mixture thereof" in this description and claims identifies any mixture of two or more compounds selected from the factors of the A/16686 complex and the derivatives thereof mentioned above, in any proportion.

When used alone and not otherwise specified, the term "ramoplanin" usually identifies the factor A2 of A/16686 or a preparation containing at least 80% (with respect to the whole antibiotic substance, by HPLC assay) of such factor A2, the remaining portion consisting essentially of small amounts of the related A and A' factors. Preparations of this type are currently obtained from pilot or semi-industrial fermentation and recovery operations.

Central venous polyurethane catheters with a thin hydrophilic coating on the surfaces which can be advantageously utilized according to this invention are described in the literature. For instance, U.S. Pat. No. 4769013 discloses a method of coating medical devices, including catheters, with a poly-N-vinylpyrrolidone-polyurethane interpolymer useful to form coated devices which can release antibacterial agents adsorbed thereon.

U.S. Pat. No. 4,950,256 reports a series of references to methods of coating medical devices, including catheters, with a thin hydrophilic layer with low friction in wet conditions and improved blood compatibility and describes an intravascular catheter coated with hydrophilic polymer having adsorbed an amount of the cationic cyclic polypeptide antibiotic polymixin sufficient to inhibit the growth of bacteria and the formation of blood clots. Polymixin is an antibiotic generally active against gram-negative bacteria.

Catheters which have been found particularly suitable for use in the embodiment of this invention are polyurethane catheters with a thin hydrophilic coating on both the internal and external surface based on a poly-N-vinylpyrrolidone-polyurethane interpolymer of approximately 200 μm thickness, marketed under the trade name Hydrocath® (Viggo-Spectramed, Swindon, Wiltshire, England).

These hydrophilic central venous catheters (which are available as single, double and triple lumen types), due to their coating, show a percent swelling after incubation at room temperature for 24 hours in water, water:ethanol 1:1 or ethanol of, respectively, 8.0, 16.1 and 30.5.

According to the method of preparing the catheter of this invention, the above mentioned polyurethane catheters coated with a hydrophilic film are incubated in an aqueous solution of an antibiotic of the ramoplanin group or any mixture thereof, preferably, ramoplanin, at a concentration varying from 1 to 50 mg/ml, preferably 5 to 30 mg/ml at a temperature between 10° C. to 60° C., preferably between 20° C. and 40° C. for a period varying from 5 minutes to 48 hours, preferably from 10 minutes to 30 hours.

During the above incubation period, relatively large amounts of antibiotic of the ramoplanin group or any mixture thereof can bind to the catheter.

Since the above parameters are generally correlated, their influence on the loading of the catheters may be evaluated by carrying out a series of loading experiments wherein the concentration of the solution of the antibiotic of the ramoplanin group or any mixture thereof, the incubation temperature and the time are varied.

An indication of the amount of the antibiotic of the ramoplanin group or any mixture thereof loaded on the catheter according to the method of this invention, may be obtained by means of incubation of the loaded catheter (after washing with demineralized water and drying overnight under vacuum) at room temperature in a 8M guanidine hydrochloride water solution, for a planned time. The amount of antibiotic eluted in the guanidine solution is then evaluated by microbiological assay. The appropriate incubation time is determined by verifying whether a second incubation period in a fresh 8M guanidine hydrochloride solution, followed by microbiological assay, shows further release of antibiotic or not. Current experiments of incubation in a 8M guanidine hydrochloride water solution have demonstrated that after the incubation period of one hour no further release of antibiotic from the loaded catheter into the fresh guanidine hydrochloride solution is observed.

When the above loading conditions are applied, the amount of antibiotic released in the 8M guanidine hydrochloride solution of incubation, when related to the catheter length, generally corresponds to a value ranging from 20 μg/cm to 100 μg/cm.

The efficacy of the central venous catheter loaded with an antibiotic of the ramoplanin group or any mixture thereof in preventing catheter related infections, was demonstrated in animal experiments. The method utilized for the above mentioned experiments is described by G. Romanò et al. (21).

Segments (1 cm) of Hydrocath® catheter (coated or uncoated with the antibiotic) were inserted subcutaneously in anesthetized mice (male and female CD-1 mice, Charles-River) 96 h, 48 h and immediately before infection. 0.1 ml of a bacterial suspension of *Staphylococcus aureus* L 1162 was injected subcutaneously in close proximity to the catheter segments. Bacterial suspensions consisted of approximately $2 \times 10^8$ CFU/ml for *S. aureus* L 1162 prepared in BBL Trypticase soy broth from overnight growth on 7% sheep blood agar plates. Twenty-four and 48 hours after infection, catheters were removed and placed individually into 5 ml of PBS.

Bacteria were then harvested from catheters. Each catheter was washed three times in 5 ml of PBS and finally covered with 2 ml of PBS in a glass tube. Bacteria adhering to the catheter were removed by sonication at 90–100 μA of two cycles of 45 seconds each with an intervening period of 3 seconds. This treatment was shown in preliminary experiments to remove all adherent bacteria, since no growth was observed around catheters placed on Difco Todd-Hewitt agar plates after sonication and it had no detrimental effects on bacterial viability. Bacteria dislodged from the catheter were subsequently diluted in PBS and 0.1 ml aliquots of suitable dilutions spread onto Difco Todd-Hewitt agar plates to determine the number of viable bacteria.

Table I and Table II report the results of the experiments on the in vivo efficacy of catheters loaded with ramoplanin in preventing colonization with *S. aureus* L 1162 compared with that of catheters loaded with teicoplanin.

TABLE I

*S. aureus* L 1162 adherence on Hydrocath® catheters inserted in the mouse 48 and 0 hours before infection

| Group | Infection (h after catheter insertion) | Extraction (h after catheter infection) | Mean $Log_{10}$ CFU/cat (SD) |
|---|---|---|---|
| Control | 0 | 24 | 4.4 (1.8) |
|  |  | 48 | 5.3 (0.9) |
|  | 48 | 24 | 4.3 (1.2) |
|  |  | 48 | 5.5 (0.6) |
| Ramoplanin | 0 | 24 | ≦1.0 (0) |
|  |  | 48 | ≦1.0 (0) |
|  | 48 | 24 | 1.9 (0.8) |
|  |  | 48 | 1.8 (1.1) |
| Teicoplanin | 0 | 24 | 1.3 (0.4) |
|  |  | 48 | 1.7 (0.8) |
|  | 48 | 24 | 2.0 (1.3) |
|  |  | 48 | 1.6 (0.9) |

TABLE II

*S. aureus* L 1162 adherence on Hydrocath® catheters inserted in the mouse 96 and 0 hours before infection

| Group | Infection (h after catheter insertion) | Extraction (h after catheter infection) | Mean $Log_{10}$ CFU/cat (SD) |
|---|---|---|---|
| Control | 0 | 24 | 5.1 (0.5) |
|  |  | 48 | 5.2 (1.2) |
|  | 96 | 24 | 4.7 (1.1) |
|  |  | 48 | 4.6 (1.1) |

TABLE II-continued

S. aureus L 1162 adherence on Hydrocath ® catheters inserted in the mouse 96 and 0 hours before infection

| Group | Infection (h after catheter insertion) | Extraction (h after catheter infection) | Mean Log$_{10}$ CFU/cat (SD) |
|---|---|---|---|
| Ramoplanin | 0 | 24 | ≦1.0 (0) |
| | | 48 | ≦1.0 (0) |
| | 96 | 24 | 2.3 (1.1) |
| | | 48 | 1.8 (0.8) |
| Teicoplanin | 0 | 24 | 2.2 (1.2) |
| | | 48 | 1.6 (1.4) |
| | 96 | 24 | 2.8 (0.9) |
| | | 48 | 2.0 (1.0) |

The results of the above experiments indicate that ramoplanin coating of catheters can prevent colonization of the catheter by S. aureus for a period of at least 144 hours after the insertion into the patient and at least 48 hours after bacterial contamination. Of particular interest was the finding that ramoplanin coating was generally more effective than teicoplanin coating, especially, when the catheter insertion was made immediately before infection.

Additional examination of the uninfected animals bearing catheters loaded with ramoplanin revealed no evidence of local inflammation confirming the good tolerability of the ramoplanin loaded central venous catheters.

REFERENCES

1. Bender J W, Hughes W T. Fatal Staphylococcus epidermidis sepsis following bone marrow transplantation. John Hopkins Med J. 1980; 146:13–15.
2. Duma R J, Warner J F, Dalton H P. Septicemia from intravenous infusions. New Engl J Med. 1977; 284:257–260.
3. Feld R, Leers W D, Curtis J.E, Bergsagel D E. Intravenous catheter infection study: a prospective trial in patients with neoplastic disease. Med Ped Oncol. 1975; 1:175–181.
4. Sugarman B, Young E J. Infections associated with prosthetic devices. CRC Press 1984, Boca Raton.
5. Evans R C, Holmes C F. Effect of vancomycin hydrochloride on Staphylococcus epidermidis biofilm associated with silicone elastomer. Antimicrob Agents Chemother. 1987; Vol. 31 (6):889–894.
6. Gristina A G, Jennings R A, Naylor P T, Myrvik Q N, Webb L X. Comparative in vitro antibiotic resistance of surface-colonizing coagulasenegative staphylococci. Antimicrob Agents Chemother. 1989; 33(6):813–816.
7. Sheth N K, Franson T R, Sohnle P G. Influence of bacterial adherence to intravascular catheters on in-vitro antibiotic susceptibility. Lancet. 1985; ii: 1266–1286.
8. Jansen By Schareina S, Treitz U, Peters G, Steinhauser H, Pulverer G., Antibiotic-containing polyurethanes for the prevention of foreign-body infections. Polym Mater Sci Eng. 1988; 59:794–797.
9. Jansen B, Schumacher-Perdreau F, Peters G, Pulverer G. New aspects in the pathogenesis and prevention of polymer-associated foreign body infections caused by coagulase-negative staphylococci. J. Investig Surg. 1989; 2:361–380.
10. Jansen B. Peters G. Leading Article: Modern strategies in the prevention of polymer-associated infections. J Hosp Infect. 1991; 19:83–88.
11. Cheng H. Manufacture and clinical employment of an antibiotic silicone rubber catheter. Eur Urol. 1988; 14:72–74.
12. Sakamoto I, Umemura U, Nakano M, Nihira H, Kitano T. Efficacy of an antibiotic-coated indwelling catheter. A preliminary report. J Biomed Mater Rs. 1985; Vol. 19: 1031–1040.
13. Sherertz R J, Foreman D M, Solomon D D. Efficacy of dicloxacillin-coated polyurethane catheters in preventing subcutaneous S. aureus infections in mice. Antimicrob Agents Chemother. 1989; 33(8):1174–1178.
14. Trooskin S Z, Donetz A p, Harvey R A. Prevention of catheter sepsis by by antibiotic bonding. Surgery 1985; 97:547–551.
15. Trooskin S Z, Donetz A p, Baxter J, Harvey J A, Greco R S. Infection resistant continuous peritoneal dialysis catheters. Nephron 1987; 46:263–267.
16. Jansen B., Kristinsson K G, Jansen S, Peters G, Pulverer G. In vitro efficacy of a central venous catheter (Secalon-Hyrocath®) complexed with iodine to prevent bacterial colonization. J Antimicrob Chemother 1992, accepted for publication.
17. Kamal G D, Pfaller M A, Rempe L E, Jebson P J E. Reduced intravascular catheter infection by antibiotic bonding. JAMA. 1991; 265(18):2364–2368.
18. Jansen B, Jansen S, Peters G, Pulverer G. In vitro efficacy of a central venous catheter (Hydrocath®) loaded with teicoplanin to prevent bacterial colonization. J. Hosp. Infect. 1992; 22:93–107.
19. Cavalleri B, Pagani H, Volpe G, Selva E, Parenti F. A-16686. A new antibiotic from Actinoplanes. Fermentation, isolation and preliminary physicochemical characteristics. J. Antibiot. 1984; 37:309–317.
20. Ciabatti R, Kettenring J. K, Winters G, Tuan G, Zerilli L, Cavalleri B. Ramoplanin /A/16686 . A new glycolipodepsipeptide antibiotic. III Structure elucidation. J. Antibiot. 1989; 42:254–267.
21. Romano G., Berti M., Goldstein B. P., and Borghi A., Efficacy of central venous catheter (Hydrocath®) loaded with teicoplanin in preventing subcutaneous staphylococcal infection in the mouse. Zbl. Bakt. 279 (1993) 426–436.

We claim:

1. A central venous catheter comprising a polyurethane catheter with a thin hydrophilic layer on the surface loaded with an antibiotic of the ramoplanin group in a concentration sufficient to inhibit the bacterial colonization of the catheter after insertion into the patient, wherein the antibiotic of the ramoplanin group is selected from the group consisting of antibiotic A/16686 factor A1, antibiotic A/16686 factor A2, antibiotic A/16686 factor A3, antibiotic A/16686 factor A'1, antibiotic A/16686 factor A'2, antibiotic A/16686 factor A'3, any of the derivatives thereof hydrogenated in the fatty acid chain, any aglycons thereof, and any mixture thereof.

2. A catheter of any of claims 1 wherein the thin hydrophilic layer is comprised of a poly-N-vinylpyrrolidone polyurethane interpolymer.

3. A catheter of claims 1 wherein the hydrophilic layer has a thickness of approximately 200 µm.

4. A catheter as in any of claims 1 wherein the antibiotic loaded is ramoplanin.

5. A catheter of claim 4 characterized in that, when incubated for one hour at room temperature in a 8M guanidine hydrochloride solution, it releases into the solution an amount of antibiotic that, when related to the catheter length, corresponds to a value ranging from 20 µg/cm to 100 µg/cm.

6. A process for preparing a central venous polyurethane catheter coated with a thin hydrophilic layer on the surface and loaded with an amount of an antibiotic of the ramoplanin group comprising incubation of the polyurethane catheter coated with the hydrophilic film in a solution of the antibiotic substance wherein the antibiotic is selected from the group consisting of antibiotic A/16686 factor A1, antibiotic A/16686 factor A2, antibiotic A/16686 factor A3, antibiotic A/16686 factor A'1, antibiotic A/16686 factor A'2, antibiotic A/16686 factor A'3, and any of the derivatives thereof hydrogenated in the fatty acid chain, any aglycons thereof, any mixture thereof; at a temperature between about 10° C. and 60° C. for a period of time between about 5 minutes and 48 hours.

7. A process according to claim 6 in which the solution of the antibiotic substance is in a concentration range from about 1 to about 50 mg/ml.

8. A process according to claim 6 in which the solution of the antibiotic substance is an aqueous solution.

9. A process according to claim 6 in which the antibiotic substance is Ramoplanin.

10. A method for preventing catheter related infection in a patient in need of there comprising the insertion of a central venous polyurethane catheter coated with a thin hydrophilic layer on the surface loaded with an amount of an antibiotic of the ramoplanin group selected from the group consisting of antibiotic A/16686 factor A1, antibiotic A/16686 factor A2, antibiotic A/16686 factor A3, antibiotic A/16686 A'1, antibiotic A/16686 factor A'2, antibiotic A/16686 factor A'3, any of the derivatives thereof hydrogenated in the fatty acid chain, any aglycons thereof, and any mixture thereof.

11. A method as in claim 10 wherein the antibiotic is ramoplanin.

12. A central venous polyurethane catheter comprising a polyurethane catheter coated with coating composition which incorporates an antibiotic substance of ramoplanin group and a hydrophilic layer.

13. A process for preparing a central venous polyurethane catheter with a hydrophilic layer on the surface of the catheter and incorporating an antibiotic substance of the ramoplanin group comprising incubation of the polyurethane catheter coated with the hydrophilic film in a solution of the antibiotic substance at a temperature between about 10° C. and 600° C. for a period of time between about 5 minutes and 48 hours.

* * * * *

UNITED STATES PATENT AND TRADEMARK OFFICE
CERTIFICATE OF CORRECTION

PATENT NO. : 5,752,941

DATED : May 19, 1998

INVENTOR(S) : Romano' et al.

It is certified that error appears in the above-identified patent and that said Letters Patent is hereby corrected as shown below:

Col. 10, line 25 reads "10° C. and 600° C." and should read --10° C and 60° C--.

Signed and Sealed this

Twenty-ninth Day of September, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,752,941
DATED : May 19, 1998
INVENTOR(S) : Gabriella Romano, et al It is certified that error appears in the above-identified patent and that said Letters Patent is hereby corrected as shown below:

On the title page, item [73]

"Assignee: Gruppo Lepetit S.p.A., Italy" should read - - Assignee: Biosearch Italia S.p.A., Gerenzano, Italy - -.

Signed and Sealed this

Sixth Day of July, 1999

Attest:

Q. TODD DICKINSON

*Attesting Officer*    Acting Commissioner of Patents and Trademarks